United States Patent
Schlummer et al.

(10) Patent No.: US 7,329,779 B2
(45) Date of Patent: Feb. 12, 2008

(54) PROCESS FOR PREPARING OPTIONALLY SUBSTITUTED ARYLSULPHONIC ANHYDRIDES

(75) Inventors: Björn Schlummer, Bonn (DE); Florian Rampf, Köln (DE); Paul Naab, Wuppertal (DE); Guido Giffels, Bonn (DE); Matthias Gotta, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 2 days.

(21) Appl. No.: 11/392,009

(22) Filed: Mar. 29, 2006

(65) Prior Publication Data
US 2006/0229468 A1 Oct. 12, 2006

(30) Foreign Application Priority Data
Apr. 6, 2005 (DE) ............ 10 2005 015 675

(51) Int. Cl.
*C07C 303/00* (2006.01)
(52) U.S. Cl. .................................... 562/872
(58) Field of Classification Search .......... 562/872
See application file for complete search history.

(56) References Cited

U.S. PATENT DOCUMENTS

| | | | | |
|---|---|---|---|---|
| 2,489,316 A | * | 11/1949 | Proell ............ | 562/872 |
| 4,115,058 A | | 9/1978 | Blumbergs | |
| 5,292,947 A | * | 3/1994 | Walker, Jr. ...... | 562/872 |

FOREIGN PATENT DOCUMENTS

| | | | |
|---|---|---|---|
| DE | 397311 | | 7/1924 |
| JP | 2001240588 A | * | 9/2001 |
| JP | 2003238522 A | * | 8/2003 |
| JP | 2003277345 A | * | 10/2003 |

OTHER PUBLICATIONS

Lewis Ed. Hawley's Condensed Chemical Dictionary 13th ed. JWiley & Sons,Inc. 1997 p. 32.*
Peterli-Roth et al. Synthesis of 6-Deaminosinefungin and (S)-6-Methyl-6-deaminosinefungin.J.Org. Chem. 1994, 59, 15, 4186-4193.*
Irwin et al. Environmental Contaminant Encyclopedia "Alkanes Entry". National Park Service Water Services Division, Water Operations Branch Jul. 1997 20 pages.*
Alkanes and Cyclolakanes. ChemGuide ; Benzene. InChem.org.*
Field, Lamar; *J. Am. Chem. Soc.* 1952, 74, pp. 394-398.
Kunieda, Norio; Oae, Shigeru; *Bull. Chem. Soc. Jpn.* 1968, 41, p. 233.
Field, Lamar; Settlage, Paul H.; *J. Am. Chem. Soc.* 1954, 76, p. 1222.
da Silva Corrêa, C.M.M.; Waters, William A.; *J. Chem. Soc. C* 1968, p. 1874.
Martin, Dieter; *Chem. Ber.* 1965, 98, p. 3286. (no abstract/translation available).
Mukaiyama, Teruaki; Kuwajima, Isao; *J. Org. Chem.* 1963, 28, p. 2024.
*Houben Weyl* vol. IX 1955, pp. 552, 553. (no abstract/translation available).
Karger, Michael Howard; Mazur, Yehuda; *J. Org. Chem.* 1971, 36, 4, pp. 528-531.
Bredereck, Hellmut, et al.; *Chem. Ber.* 1960, 93, p. 2736. (no abstract/translation available).
Eglinton, G., et al.; *J. Chem. Soc. Rev.* 1954, p. 1860.
*Tetrahedron Lett.* 1998, 39, 19, pp. 2919-2920.
Peterli-Roth, Patricia, et al.; *J. Org. Chem.* 1994, 59, 15, pp. 4186-4193.
Thuneberg, L.; "Synthesis of 358 p-toluenesulfonic anhydride (tosan) of high specific activity", *Intern. Appl. Radiation Isotopes*, 16(7), pp. 413-418, 1965.
Meyer, Hans; Schiege, Karl; "Anhydrides of aromatio sulphonic acids", *Monatshefte FÜr Chemie*, Bd. 34, pp. 561-577, 1913.

* cited by examiner

*Primary Examiner*—Yvonne Eyler
*Assistant Examiner*—MLouisa Lao
(74) *Attorney, Agent, or Firm*—Michael A. Miller

(57) ABSTRACT

The present invention relates to a process for preparing optionally substituted arylsulphonic anhydrides of the general formula (I)

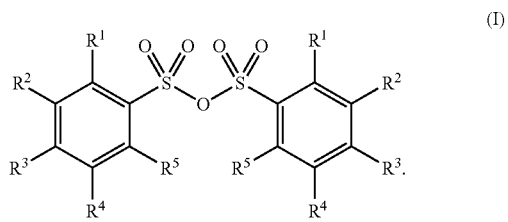

(I)

9 Claims, No Drawings

PROCESS FOR PREPARING OPTIONALLY SUBSTITUTED ARYLSULPHONIC ANHYDRIDES

The present invention provides a process for preparing optionally substituted arylsulphonic anhydrides.

p-Toluenesulphonic anhydride, for example, is a frequently used reagent for preparing p-toluenesulphonate derivatives. The resulting compounds find various uses as intermediates in pharmaceutical, agrochemical and further fields of fine chemicals chemistry. The advantage of the use of p-toluenesulphonic anhydride over other reagents for preparing toluenesulphonates is the mild reaction conditions, especially the neutral pH during the reaction, which is not the case, for example, when p-toluenesulphonyl chloride is used.

The literature describes some processes for preparing p-toluenesulphonic anhydride, for example.

*J. Am. Chem. Soc.* 1952, 74, 394-398 describes the preparation by reaction of phosphorus pentoxide, celite and asbestos with p-toluenesulphonic acid at 125° C. To isolate the product, the reaction mixture is recrystallized from benzene/diethyl ether.

A disadvantage of this reaction is the formation of polymeric phosphate derivatives which greatly complicate industrial-scale performance. *Bull. Chem. Soc. Jpn.* 1968, 41, 233 describes the preparation by reaction of bis-p-tolyldisulphane with dinitrogen tetroxide in tetrachloromethane. *J. Am. Chem. Soc.* 1954, 76, 1222 describes the preparation by reaction of p-toluenesulphonyl chloride with mercury oxide in tetrachloroethane. The recrystallization is effected from benzene/diethyl ether. *J. Chem. Soc. C* 1968, 1874 describes the preparation by reaction of p-toluenesulphonyl iodide with copper in tetrachloromethane. One disadvantage of this process is the use of the expensive iodine salt. *Chem. Ber.* 1965, 98, 3286 describes the preparation by reaction of p-toluenesulphonic acid with phenyl cyanate in benzene, a disadvantage of this process being the use of the expensive phenyl cyanate. *J. Org. Chem.* 1963, 28, 2024 describes the preparation by reaction of p-toluenesulphonic acid with diphenylmercury and tributylphosphine in benzene. *Houben Weyl vol. IX* 1955, 553 describes the preparation by reaction of anhydrous p-toluenesulphonic acid with di-p-tolylcarbodiimide in benzene. One disadvantage of this method is likewise the use of the expensive di-p-tolylcarbodiimide.

An additional disadvantage common to all of these processes is the use of toxic reagents and solvents, some of them carcinogenic and dangerous.

DE 397311 describes the preparation by reaction of p-toluenesulphonyl chloride with sodium chloride in glacial acetic acid/water at 125° C. However, hydrolysis of the product is to be expected owing to the aqueous reaction conditions.

*J. Org. Chem.* 1971, 36, 4, 528-531 describes the preparation by reaction of anhydrous p-toluenesulphonic acid with succinyl dichloride at 80° C. and subsequent application of high vacuum, and also extraction of the product with diethyl ether. However, the process is unsuitable for an industrial-scale reaction.

U.S. Pat. No. 4,115,058 describes the preparation by reaction of toluene with sulphur trioxide in nitromethane at 0° C. Disadvantages of this process are the use of the highly reactive sulphur trioxide and of the dangerous nitromethane, and also the formation of positional isomers in the reaction.

*Chem. Ber.* 1960, 93, 2736 describes the preparation by reaction of p-toluenesulphonyl chloride with silver p-toluenesulphonate in dichloromethane over three days. Disadvantages of this process are the use of the expensive silver salt and also the excessively long reaction time.

*J. Chem. Soc. Rev.* 1954, 1860. describes the preparation by reaction of p-toluenesulphonic acid with methoxyacetylene. The disadvantage here is the use of the unstable methoxyacetylene which is difficult to obtain.

*Tetrahedron Lett.* 1998, 39, 19, 2919-2920 describes the preparation by reaction of p-toluenesulphonyl chloride with p-toluenesulphonic acid in dichloromelthane by stirring at 20° C. However, the published results have not been confirmed in the reproduction of the synthesis.

*Houben Weyl vol. IX* 1955, 552 describes the preparation by reaction of anhydrous p-toluenesulphonic acid with thionyl chloride without solvent. The product should be isolated from ice-water. However, the process described was not reproducible.

*J. Org. Chem.* 1994, 59, 15, 4186-4193 describes the preparation by reaction of p-toluenesulphonic acid with thionyl chloride in benzene. However, a disadvantage of this process is again the use of carcinogenic benzene.

There is therefore still a need for an efficient synthesis also performable on the industrial scale for arylsulphonic anhydrides, especially p-toluenesulphonic anhydride, which does not have the disadvantages described above.

It is thus an object of the present invention to provide such an efficient process for preparing arylsulphonic anhydrides, especially p-toluenesulphonic anhydride, in which the desired products can be obtained in a yield sufficient for industrial-scale performance, especially avoiding toxic and carcinogenic or dangerous substances or solvents.

It has been found that, surprisingly, the reaction of the corresponding arylsulphonic acids with thionyl chlorides using aliphatic hydrocarbons as solvents leads to arylsulphonic anhydrides in good yields. This is unexpected especially taking into account the poor solubilities of the arylsulphonic acids.

The present invention therefore provides a process for preparing arylsulphonic anhydrides of the general formula (I),

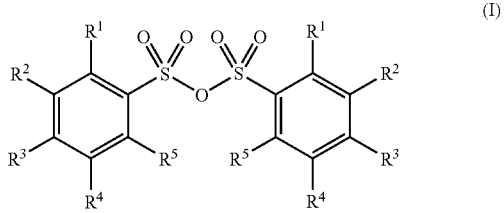

in which $R^1$ to $R^5$ are each independently hydrogen, $C_1$-$C_{12}$-alkyl, preferably $C_1$-$C_6$-alkyl, $C_1$-$C_{12}$-fluoroalkyl, preferably $C_1$-$C_6$-fluoroalkyl, $C_1$-$C_{12}$-alkoxy, preferably $C_1$-$C_6$-alkoxy, $C_1$-$C_{12}$-fluoroalkoxy, preferably $C_1$-$C_6$-fluoroalkoxy, $C_4$-$C_{18}$-aryl, preferably $C_5$-$C_{10}$-aryl, or $C_5$-$C_{19}$-arylalkyl, halogen or $NO_2$, wherein arylsulphonic acids of the general formula (II),

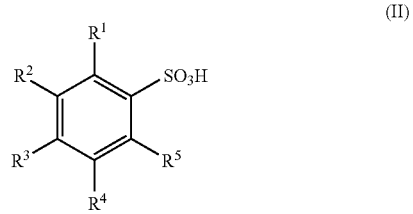

(II)

in which $R^1$ to $R^5$ are each as defined for the general formula (I), are reacted with thionyl chloride in at least one optionally substituted aliphatic hydrocarbon as solvent.

The solvents used may be cyclic or acyclic aliphatic hydrocarbons or mixtures thereof. Examples of suitable cyclic or acyclic aliphatic hydrocarbons are cyclopentane, cyclohexane, methylcyclohexane, cycloheptane, cyclooctane, hexane, heptane, octane and petroleum ether. Preference is given to cyclic hydrocarbons, particular preference to cyclopentane, cyclohexane, methylcyclohexane or mixtures thereof.

Thionyl chloride is used in excess based on the amount of the arylsulphonic acid of the general formula (II) used. Preference is given to excesses of 1.5 to 5 equivalents, particular preference to excesses of 2 to 3 equivalents.

The scope of the invention encompasses all radical definitions, parameters and illustrations above and listed below, in general or within areas of preference, with one another, i.e. also between the particular areas and areas of preference in any combination.

Alkyl and alkoxy each independently represent a straight-chain, cyclic, branched or unbranched alkyl and alkoxy radical respectively, and the radicals mentioned may be further substituted. The same applies to the alkylene moiety of an arylalkyl radical.

$C_1$-$C_6$-Alkyl is, for example and with preference, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl; $C_1$-$C_{12}$-alkyl is additionally, for example, n-heptyl, n-octyl, n-decyl and n-dodecyl.

$C_1$-$C_6$-Alkoxy is, for example and with preference, methoxy, ethoxy, n-propoxy, isopropoxy, n-butoxy, sec-butoxy, tert-butoxy, n-pentoxy, cyclohexoxy, cyclopentoxy, n-hexoxy; $C_1$-$C_{12}$-alkoxy is additionally, for example, n-heptoxy, n-octoxy, n-decoxy and n-dodecoxy.

Fluoroalkyl and fluoroalkoxy are each independently a straight-chain, cyclic, branched or unbranched alkyl radical and alkoxy radical respectively, which is singly, multiply or fully substituted by fluorine atoms.

For example, $C_1$-$C_{12}$-fluoroalkyl is trifluoromethyl, 2,2,2-trifluoroethyl, pentafluoroethyl, nonafluorobutyl, heptafluoroisopropyl, perfluorooctyl and perfluorododecyl.

For example, $C_1$-$C_{12}$-fluoroalkoxy is trifluoromethoxy, 2,2,2-trifluoroethoxy, pentafluoroethoxy, nonafluorobutoxy, heptafluoroisopropoxy, perfluorooctoxy and perfluorododecoxy.

Aryl is in each case a mono-, bi- or tricyclic heteroaromatic radical having 5 to 18 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen, or preferably a mono-, bi- or tricyclic carbocyclic aromatic radical having 5 to 18, preferably 6 to 10 skeleton carbon atoms.

Examples of mono-, bi- or tricyclic carbocyclic aromatic radicals having 5 to 18 skeleton carbon atoms are phenyl, biphenylyl, naphthyl, phenanthrenyl, anthracenyl or fluorenyl, mono-, bi- or tricyclic heteroaromatic radicals having 5 to 18 skeleton carbon atoms, in which no, one, two or three skeleton carbon atoms per cycle, but at least one skeleton carbon atom in the entire molecule, may be substituted by heteroatoms selected from the group of nitrogen, sulphur or oxygen, are, for example, pyridinyl, oxazolyl, benzofuranyl, dibenzofuranyl or quinolinyl.

In addition, the carbocyclic aromatic radical or heteroaromatic radical may be substituted by up to five identical or different substituents per cycle which are selected from the group of halogen, cyano, $C_1$-$C_{12}$-alkyl, $C_1$-$C_{12}$-fluoroalkyl, $C_1$-$C_{12}$-fluoroalkoxy or $C_1$-$C_{12}$-alkoxy.

Arylalkyl is in each case independently a straight-chain, cyclic, branched or unbranched alkyl radical as defined above, which may be substituted singly, multiply or fully by aryl radicals as defined above. One example of arylalkyl radicals is benzyl.

Halogen is fluorine, chlorine, bromine or iodine, preferably fluorine, chlorine or bromine.

The process according to the invention is preferentially suitable for preparing the arylsulphonic anhydride of the general formula (I) in which $R^1$, $R^2$, $R^4$ and $R^5$ are each H and $R^3$ is methyl, i.e. for the preparation of p-toluenesulphonic anhydride.

The process according to the invention can be carried out in such a way that the arylsulphonic acid of the general formula (II) is initially charged in at least one solvent and the thionyl chloride is added. Alternatively, the thionyl chloride may also be initially charged in at least one solvent and the arylsulphonic acid of the general formula (II) added. A further alternative consists in the concerted addition of the two reactants in at least one solvent. Any combinations of these alternatives are possible.

In some cases, it may also be advantageous to heat the reaction mixture in the case of initial charging of arylsulphonic acid of the general formula (II) before addition of the thionyl chloride or in the case of initial charging of the thionyl chloride before addition of the arylsulphonic acid of the general formula (II). Preference is given to heating to temperatures of 25 to 100° C. Particular preference is given to temperatures of 40 to 80° C., very particular preference to temperatures of 45 to 65° C.

In some cases, it may be advantageous to continue to stir the reaction mixture at the reaction temperature after full addition or combination. Preference is given to continuing to stir in this way for a period of 0.1 to 5 h, more preferably 0.5 to 3 h, most preferably 0.5 to 1 h.

The excess thionyl chloride can optionally be distilled out of the reaction mixture after the continued stirring time. The distillation is carried out at bottom temperatures of 70 to 100° C., preferably 75 to 90° C., more preferably 80 to 85° C. The distillation can be carried out at ambient pressure (standard pressure) or reduced pressure. In preferred embodiments, distillation is effected at standard pressure. Recycling of the thionyl chloride distilled off into the reaction process is possible.

The desired arylsulphonic anhydride of the general formula (I) is isolated preferably by means of precipitation by cooling the reaction mixture, optionally after the excess thionyl chloride has been distilled off. After the cooling, it may additionally be advantageous to continue to stir the reaction mixture at this temperature. The precipitation is effected, for example, by cooling to +20° C. or at least one temperature below +20° C. Preference is given to cooling to at least one temperature of −10 to +20° C., more preferably temperatures of 0 to 10° C. Very particular preference is given to 5° C. The continued stirring can be effected for a period of 0.1 to 5 h, more preferably 0.5 to 3 h, most preferably 1 h.

In a preferred variant, the process according to the invention is carried out in such a way that the arylsulphonic acid of the general formula (II) is initially charged in at least one solvent, the reaction mixture is heated and the thionyl chloride is added to this heated reaction solution. After addition has ended, the reaction mixture continues to be stirred. Subsequently, excess thionyl chloride is distilled off and the reaction mixture is cooled. The resulting arylsulphonic anhydride is filtered off with suction and dried by passing protective gas over it.

The advantage of the process according to the invention is that the carcinogenic solvent benzene and also further toxic, expensive and/or dangerous substances can be dispensed with and the desired arylsulphonic anhydrides of the general formula (I) are obtained in good yields sufficient for industrial-scale application.

The examples which follow serve to illustrate the invention by way of example and are not to be interpreted as a restriction.

EXAMPLES

Example 1

Preparation of p-toluenesulphonic anhydride in methylcyclohexane as a Solvent 50.0 g (260 mmol) of p-toluenesulphonic acid monohydrate were suspended in 140 g of methylcyclohexane and heated to 50° C. with stirring. 99.9 g (831 mmol, 3.2 equivalents [eq.]) of thionyl chloride were then added dropwise over a period of 75 minutes at such a rate that moderate gas evolution was observed. After addition had ended, the mixture was stirred at 50° C. for a further 1 h. 20.1 g of excess thionyl chloride were then distilled off at a bottom temperature of 96° C. The residue was cooled to 5° C. and stirred at this temperature for 1 h. The precipitated solid was filtered off and washed with 50 ml of methylcyclohexane. After drying under reduced pressure, 22.2 g (52% of theory) of p-toluenesulphonic anhydride were isolated.

Melting point: 118-120° C., content: 95.6% by weight ($^1$H NMR).

Example 2

Preparation of p-toluenesulphonic anhydride in cyclohexane as a Solvent 150.0 g (789 mmol) of p-toluenesulphonic acid monohydrate were suspended in 360 g of cyclohexane and heated to 50° C. with stirring. 240.0 g (1997 mmol, 2.6 eq.) of thionyl chloride were then added dropwise over a period of 190 min at such a rate that moderate gas evolution was observed. After addition had ended, the mixture was stirred at 50° C. for a further 0.5 h. 80 g of excess thionyl chloride/cyclohexane were then distilled off at a bottom temperature of 71-76° C. The residue was cooled to 5° C. and stirred at this temperature for 1 h. The precipitated solid was filtered off and washed with 150 ml of cyclohexane. After drying under reduced pressure, 70.5 g (53% of theory) of p-toluenesulphonic anhydride were isolated.

Melting point: 123-124° C., content: 96.1% by weight ($^1$H NMR).

The invention claimed is:

1. Process for preparing arylsulphonic anhydrides of the general formula (I),

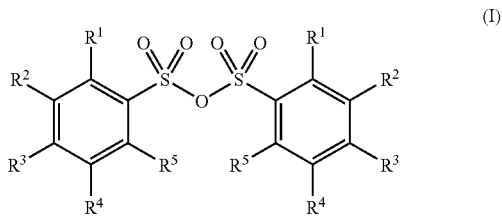

(I)

in which
$R^1$ to $R^5$ are each independently hydrogen, $C_1$-$C_{12}$-alkyl, $C_1$-$C_{12}$-fluoroalkyl, $C_1$-$C_{12}$-alkoxy, $C_1$-$C_{12}$-fluoroalkoxy, $C_4$-$C_{18}$-aryl or $C_5$-$C_{19}$-arylalkyl, halogen, $NO_2$,
wherein arylsulphonic acids of the general formula (II),

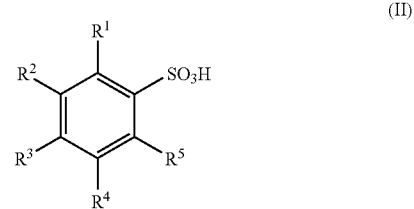

(II)

in which $R^1$ to $R^5$ are each as defined for the general formula (I),
are reacted with thionyl chloride in at least one optionally substituted cyclic or acyclic aliphatic hydrocarbon as a solvent.

2. Process according to claim 1, wherein the solvent used is at least one optionally substituted cycloaliphatic hydrocarbon.

3. Process according to claim 1, wherein the solvent used is cyclopentane, cyclohexane, methylcyclohexane or mixtures thereof.

4. Process according to claim 1, wherein $R^1$, $R^2$, $R^4$ and $R^5$ are each H and $R^3$ is methyl.

5. Process according to claim 1, wherein thionyl chloride is used in excess based on the amount of the sulphonic acid of the general formula (II).

6. Process according to claim 1, wherein the sulphonic acid of the general formula (II) is initially charged in the solvent(s) and heated to temperatures of 25 to 100° C., and the thionyl chloride is added to this heated reaction solution.

7. Process according to claim 1, wherein the reaction mixture, after addition of the thionyl chloride, is stirred further for a period of 0.1 to 5 h.

8. Process according to claim 1, wherein the excess thionyl chloride is optionally distilled out of the reaction mixture after the continued stirring time.

9. Process according to claim 1, wherein the arylsulphonic anhydride of the general formula (I) is optionally precipitated out by cooling the reaction mixture to +20° C. or at least one temperature below +20° C. after the excess thionyl chloride has been distilled off.

* * * * *